(12) United States Patent
Truitt et al.

(10) Patent No.: US 6,915,705 B1
(45) Date of Patent: Jul. 12, 2005

(54) FLOW SENSOR AND FLOW RESISTIVE ELEMENT

(75) Inventors: Patrick W. Truitt, Pittsburgh, PA (US); Michael Bobeck, Sarver, PA (US)

(73) Assignee: RIC Investments, Inc., Wilmington, DE (US)

( * ) Notice: Subject to any disclaimer, the term of this patent is extended or adjusted under 35 U.S.C. 154(b) by 0 days.

(21) Appl. No.: 10/401,435

(22) Filed: Mar. 28, 2003

Related U.S. Application Data

(60) Provisional application No. 60/369,708, filed on Apr. 3, 2002.

(51) Int. Cl.⁷ .................................................. G01F 1/37
(52) U.S. Cl. .................................................. 73/861.52
(58) Field of Search ........................ 73/861.52, 861.42, 73/861.77, 861.79

(56) References Cited

U.S. PATENT DOCUMENTS

| | | |
|---|---|---|
| 4,083,245 A | 4/1978 | Osborn |
| 4,178,919 A | 12/1979 | Hall |
| 4,413,530 A | 11/1983 | Guadagnin et al. |
| 4,506,553 A | 3/1985 | Bruce et al. |
| 4,523,481 A | 6/1985 | Steen |
| 4,548,076 A | 10/1985 | Haake et al. |
| 4,599,895 A | 7/1986 | Wiseman |
| 4,754,651 A | 7/1988 | Shortridge et al. |
| 4,796,651 A | 1/1989 | Ginn et al. |
| 4,905,709 A | 3/1990 | Bieganski et al. |
| 5,033,312 A | 7/1991 | Stupecky |
| 5,038,621 A | 8/1991 | Stupecky |
| 5,060,655 A | 10/1991 | Rudolph |
| 5,107,860 A | 4/1992 | Malouvier et al. |
| 5,137,026 A | 8/1992 | Waterson et al. |
| 5,313,955 A * | 5/1994 | Rodder ....................... 600/538 |
| 5,357,972 A | 10/1994 | Norlien |
| 5,357,975 A | 10/1994 | Kraemer et al. |
| 5,450,760 A * | 9/1995 | Lew et al. ............... 73/861.77 |
| 5,535,739 A | 7/1996 | Rapoport et al. |
| 5,546,933 A | 8/1996 | Rapoport et al. |

(Continued)

FOREIGN PATENT DOCUMENTS

| | | |
|---|---|---|
| EP | 0 086 259 A2 | 11/1981 |
| EP | 0 772 026 A2 | 5/1997 |

OTHER PUBLICATIONS

Tatara et al., "An Apnea Monitor Using a Rapid-Response Hygrometer", Journal of Clinical Monitoring, 1997, pp. 5-9, vol. 13, Kluwer Academic Publishers, Netherlands.

(Continued)

Primary Examiner—Edward Lefkowitz
Assistant Examiner—Corey D. Mack
(74) Attorney, Agent, or Firm—Michael W. Haas

(57) ABSTRACT

A flow sensor is disclosed that measures a flow of fluid passing through a conduit and a flow resistive element for use in such a flow sensor. The flow sensor includes a housing having a main channel defined therethrough. A flow resistive element is disposed in the housing across the main channel. The flow resistive element includes a rigid body member having a first surface and a second surface. A plurality of unobstructed, wedge-shaped, openings are defined in the body member and extend through the rigid body member. In addition, a plurality of spokes extend from a central portion of the body member to its perimeter so that each spoke separates adjacent wedge-shaped openings from one another.

22 Claims, 10 Drawing Sheets

U.S. PATENT DOCUMENTS

| | | |
|---|---|---|
| 5,722,417 A | 3/1998 | Garbe |
| 5,743,270 A | 4/1998 | Gazzara et al. |
| 5,803,066 A | 9/1998 | Rapoport et al. |
| 6,017,315 A | 1/2000 | Starr et al. |
| 6,119,723 A | 9/2000 | Kenyon |
| 6,644,132 B1 * | 11/2003 | Baumoel ................. 73/861.72 |

OTHER PUBLICATIONS

Berghuis et al., "Biophysical Measurement Series: Respiration", 1992, pp. 55-67, SpaceLabs, Inc., Washington, USA.

* cited by examiner

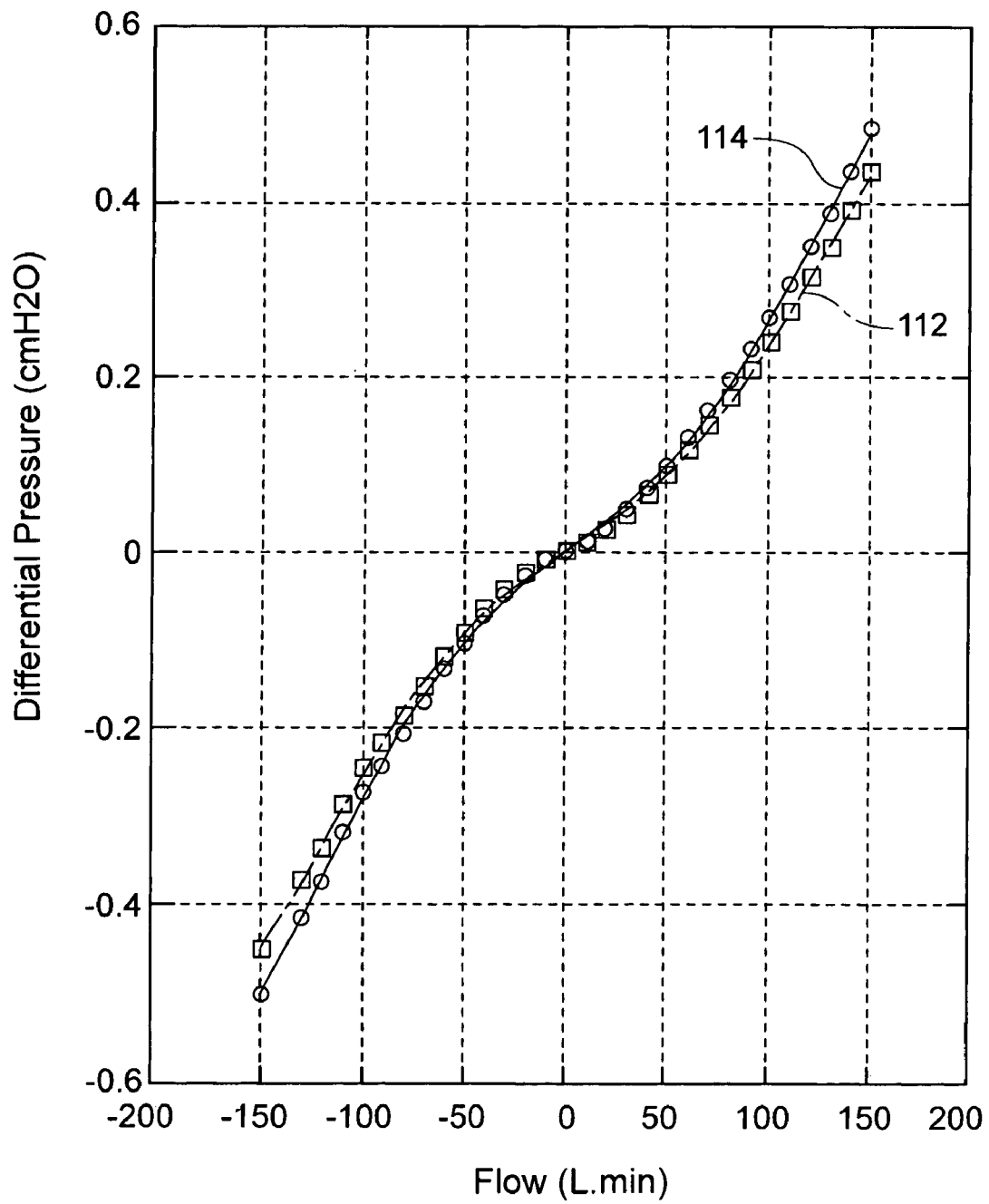

FLOW SENSOR AND FLOW RESISTIVE ELEMENT

CROSS-REFERENCE TO RELATED APPLICATIONS

This application claims priority under 35 U.S.C. § 119(e) from provisional U.S. patent application No. 60/369,708 filed Apr. 3, 2002.

BACKGROUND OF THE INVENTION

1. Field of the Invention

The present invention pertains to a flow sensor for measuring the flow of fluid through a conduit, and, in particular, to a flow sensor having a flow resistive element and housing supporting the flow resistive element that optimizes the performance of the flow sensor while minimizing its components and cost.

2. Description of the Related Art

There are numerous situations where it is desirable to measure the flow of fluid passing through a conduit. For example, it is known to assess the pulmonary function of a patient by monitoring the flow and volume of fluid inhaled and exhaled by that patient using a spirometer. In its simplest form, a spirometer is a fluid carrying conduit that the patient breathes into, and a flow sensor for measuring the flow of fluid passing through the conduit. Examples of conventional spirometers are taught in U.S. Pat. Nos. 5,107,860 to Malouvier et al., 5,137,026 to Waterson et al., and 5,722,417 to Garbe.

It is also known to treat a breathing disorder, such as sleep apnea, with a pressure support system that delivers a flow of breathing gas to the airway of a patient at an elevated pressure. A typical conventional pressure support system 30 is shown in FIG. 1 and includes a pressure generating system 32 and a patient circuit 34, which includes a conduit 36 and a patient interface 38. Pressure generating system 32 receives a supply of breathing gas, such as air, and elevates the pressure of the breathing gas at its output to a pressure that is greater than atmospheric pressure for delivery to the patient.

Depending on its operating capabilities, pressure generating system 32 may include a pressure control system to control the pressure of fluid delivered to the patient. Examples of suitable pressure control mechanisms include (1) a pressure control valve 40 downstream of the pressure generator, (2) a variable speed motor 42 associated with pressure generator 32, or both to vary the pressure output by the pressure generator. The pressure control valve and variable speed motor typically operate under the control of a control unit 44 in a feedback fashion based on signals from sensors associated with the patient circuit. A pressure support system that provides a variable pressure to the patient based on patient's respiratory cycle, for example, is taught in U.S. Pat. Nos. 5,148,802 and 5,433,193, both to Sanders et al., the contents of which are incorporated by reference into the present application.

Typically, a flow sensor 46 is provided to measure a rate at which the breathing gas flows within conduit 36. It is also known to provide a pressure sensor 48 that detects the pressure of the gas in the patient circuit or at the patient. In the illustrated embodiment, pressure sensor 48 is in fluid communication with patient interface device 38 via conduit 36. A conventional pressure support system typically includes an input/output interface device 50, such as a keypad and/or display, for communicating, information, data and/or instructions between the user and control unit 44.

Numerous sensors exist that function as flow sensor 46, i.e., to measure the flow of fluid in the patient circuit. For example, it is known to use a pneumotach flow meter placed directly in the patient circuit to measure the flow of fluid. Examples of conventional flow meters are taught in U.S. Pat. Nos. 4,083,245 to Osborn; 4,796,651 to Ginn et al.; 4,905,709 to Bieganski et al.; 4,989,456; 5,033,312 and 5,038,621 all to Stupecky; and 5,357,792 to Norlien et al.

It should be noted that the term "fluid" as used herein refers to any gas, including a gas mixture or a gas with particles, such as an aerosol medication, suspended therein. Most commonly, the fluid delivered to a patient by a pressure support system is pressurized air.

As with the spirometers noted above, a conventional flow sensor typically includes a conduit having a flow element disposed in the conduit to provide a known resistance to flow through the sensor, thereby creating a pressure differential across the flow element. In a first type of conventional flow sensor, most of the fluid flowing through the sensor passes through the flow element, and the pressure differential created by the flow element causes a lesser portion of the gas passing through the sensor to be diverted through a bypass channel connected across the flow element. An airflow sensor in the bypass channel measures the flow of gas passing therethrough. Because the area of the flow element and the area of the bypass channel are known and fixed relative to one another, the amount of gas flowing through the bypass channel is a known fraction of the total gas flow delivered to the flow sensor. Thus, the flow of fluid through the flow sensor is determined from the bypass flow measurement.

In a second type of conventional flow sensor, a pressure sensor, rather than an airflow sensor, is provided in the bypass channel. Gas does not pass through the pressure sensor. Instead, each side of a diaphragm in the pressure sensor communicates with respective pressures on either side of the flow element. The pressure sensor measures the pressure differential across the flow element to determine the rate of flow of gas through the flow sensor.

A common goal of conventional flow sensors is to provide a linear relationship between the flow of fluid through the sensor and the pressure difference developed across the flow element as a result of this flow. To this end, numerous conventional flow sensors employ a flow element that has a variable geometry, such as bending flaps, that alter their shape, and, hence, the pressure-flow relation, based on the rate of flow through the flow sensor.

Yet another goal of conventional flow sensors is to provide a laminar flow of fluid through the sensor, because turbulent flow can produce erroneous flow measurements, especially if the turbulence is located at the point in the flow sensor where the pressure sensor or mass airflow sensor communicates with the primary flow of gas through the flow sensor. To this end, it is known to employ flow element in the flow sensor that is comprised of a large number of honey-comb like channels that extend in the direction of gas flow. These numerous channels straighten or make laminar the flow of gas through the flow element, thereby preventing or minimizing turbulence.

A significant disadvantage of flow sensors that use a variable orifice (flexible obstruction) flow element is the complexity of such designs. That is, the bending elements must be precisely manufactured and assembled to produce the correct pressure-flow relationship. In addition, some of these types of flow sensor are position dependent and may produce turbulent flow due to their lack of flow laminarizing elements.

A significant disadvantage of conventional flow sensors that attempt to make laminar the flow of fluid through the flow element is the complexity and cost of manufacturing a flow element having a large number of a honey-comb like channels. Also, these channels are prone to clogging, and often provide a less than ideal pressure-flow relationship.

SUMMARY OF THE INVENTION

Accordingly, it is an object of the present invention to provide a flow sensor that overcomes the shortcomings of conventional flow sensors. This object is achieved according to one embodiment of the present invention by providing a flow sensor that includes a housing having a first end, a second end, and a main channel defined through the housing between the first end and the second end. The main channel includes a longitudinal axis, and the first and the second ends of the housing are adapted to be coupled to the conduit so that fluid passes through the housing along the main channel between the first and second ends. A flow resistive element is disposed in the housing so as to traverse the main channel. The flow resistive element of the present invention comprises a rigid body member having a first surface and a second surface. A plurality of unobstructed, wedge-shaped, openings are defined in the body member and extend through the body member from its first surface to its second surface. Each wedge-shaped opening is separated from one another by a spoke extending from a central portion of the body member to the perimeter of the body member.

It is a further object of the present invention to provide a flow restrictive element that does not suffer from the above-described disadvantages of conventional flow restrictive elements in a conventional flow sensor. This object is achieved according to the present invention by providing a flow restrictive element that includes a rigid body member having a first surface and a second surface and a longitudinal axis. A plurality of unobstructed, wedge-shaped, openings are defined in the body member and extend therethrough from its first surface to its second surface. Finally, a plurality of spokes extend from a central portion of the body member to a perimeter of the body member. Each spoke separates adjacent wedge-shaped openings from one another.

As a result of the configuration for the flow sensor and flow resistive elements summarized above, the flow sensor of the present invention provides a relatively linear pressure-flow relation while also maintaining a relatively laminar flow through the flow sensor. In addition, these objects are accomplished using relatively inexpensive components that are easy to manufacture and assembly.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 8 is a chart illustrating the pressure versus flow relationship of the flow sensor of FIG. 2;

DETAILED DESCRIPTION OF THE PRESENTLY PREFERRED EXEMPLARY EMODIMENTS

Figure 1:
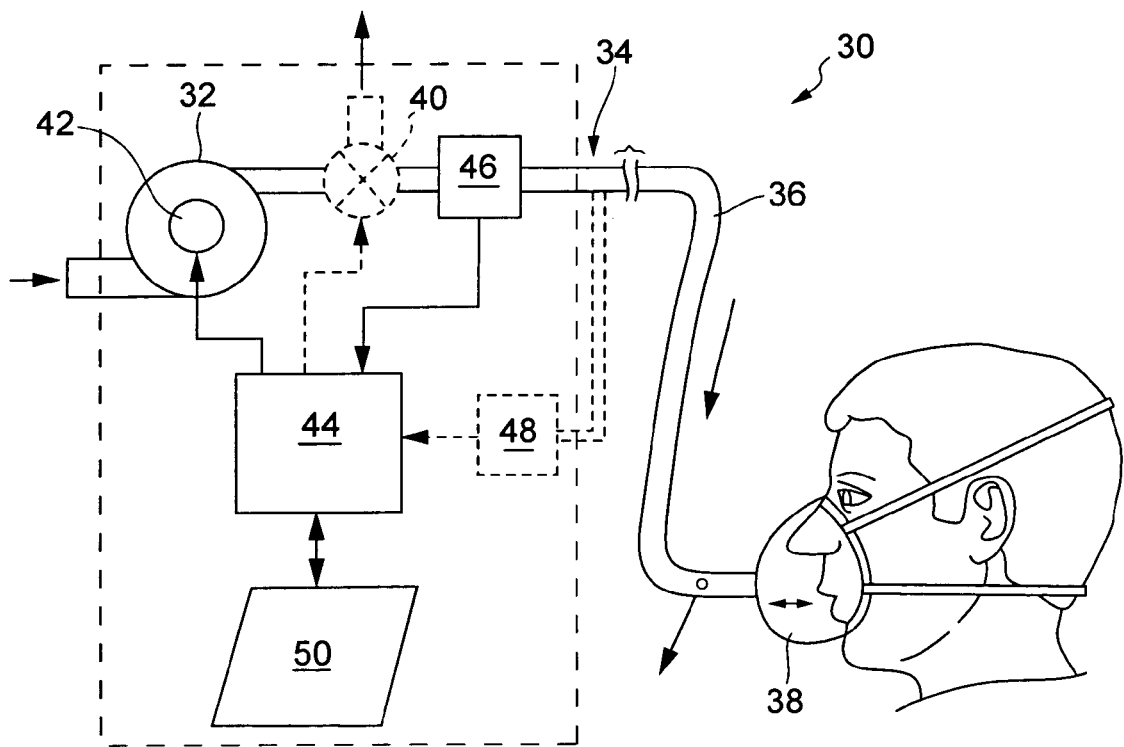
FIG. 1 is a schematic illustration of a conventional pressure support system in which the flow sensor of the present invention is suitable for use.

The general configuration of a flow sensor 50 in accordance with the principles of the present invention is described in below with reference to FIGS. 2–7. Flow sensor 50 is suitable for use in any application where the flow of fluid is to be measured. However, the present invention contemplates using flow sensor 50 in a pressure support system, such as that shown in FIG. 1, or in a spirometer.

Flow sensor 50 includes a housing 52 defined by a first housing portion 54 and a second housing portion 56 that are coupled together. A main channel 58 is defined along a longitudinal axis 60 of the housing and extends through the housing. Housing 52 includes a first end at first housing portion 54 and a second end at second housing portion 56 that are sized, configured and arranged to couple to a patient circuit in a pressure support system so that the flow sensor is providing in-line with the flow of gas through the patient circuit. That is, all gas flowing through the patient circuit must pass through the flow sensor generally along the main channel through the housing.

In the illustrated exemplary embodiment, first housing portion 54 and second housing portion 56 are identical in size, shape, and structure. This provides a manufacturing advantage in that the flow sensor requires fewer parts than conventional flow sensors having separately configured first and second housing portions. In addition, the first and second housing portions contain all of the elements of a locking assembly 62 that couples these two portions together. In the illustrated embodiment the locking assembly is a snap-type configuration where an angled member 64 snaps into an engaged relation with a receiving member 66. By providing a locking assembly on the first and second housing portions, the present invention eliminates the need for other parts, such as locking ring to join the components of the housing. In addition, the snap-type locking assembly of the present invention is easy to assembly and provides a secure attachment of the two portions of the housing.

Figure 2:
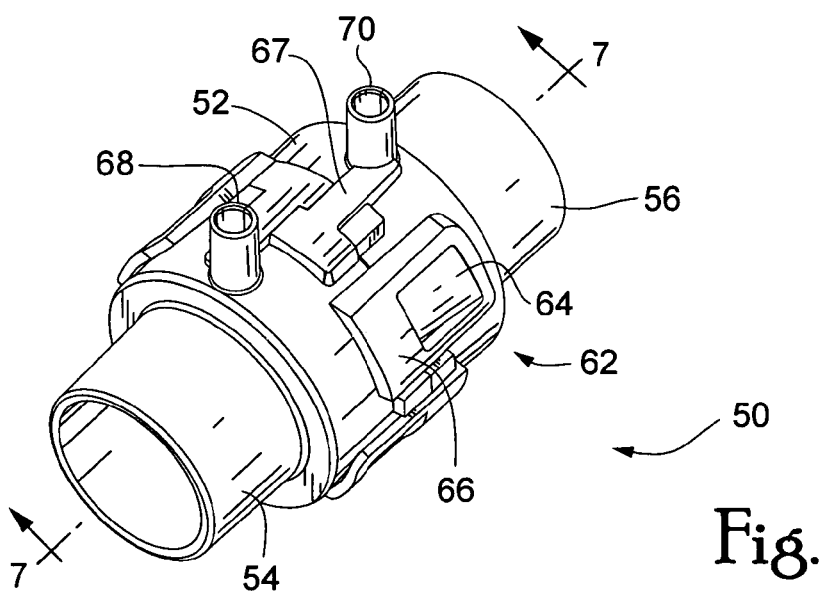
FIG. 2 is a perspective view of a first embodiment of a flow sensor according to the principles of the present invention.
Figure 3:
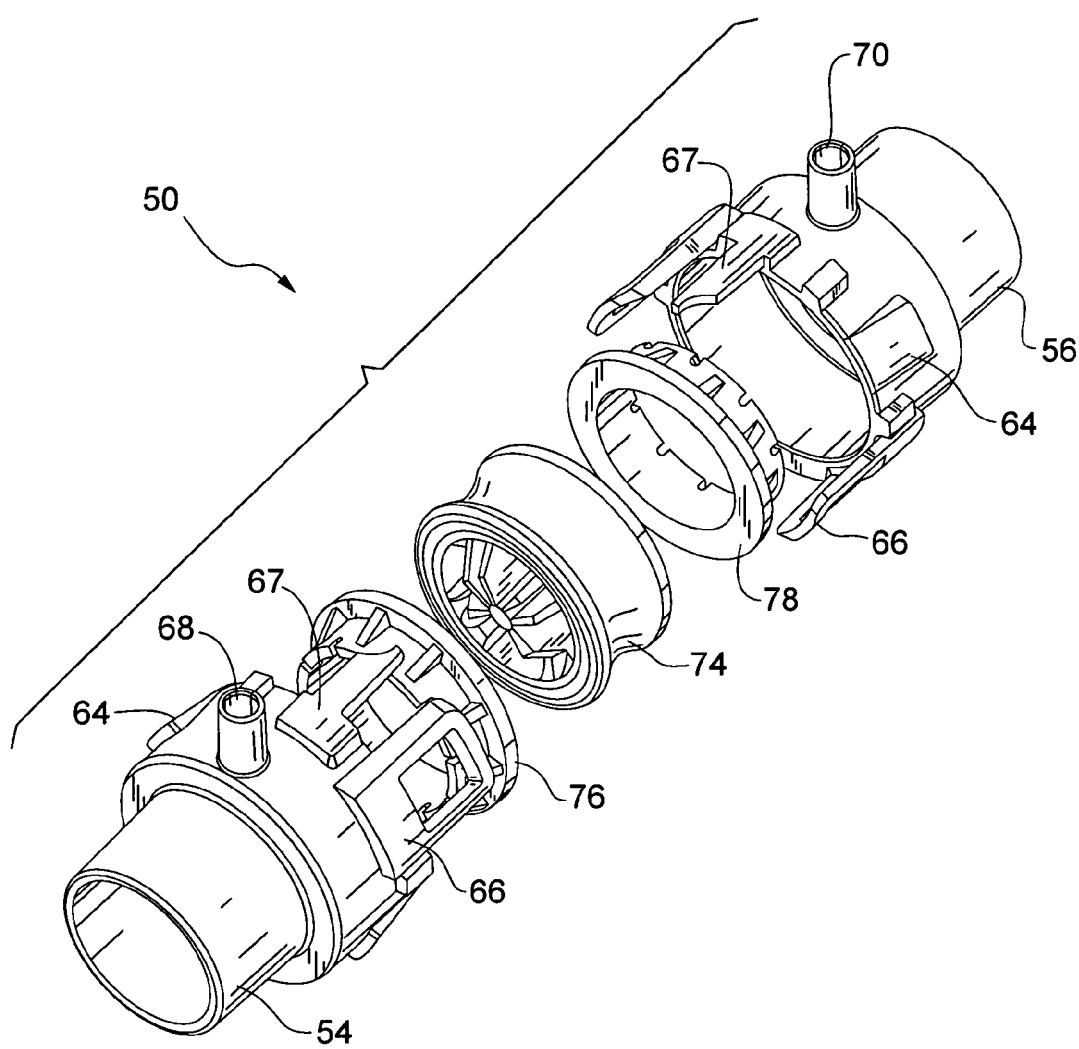
FIG. 3 is an exploded view of the flow sensor of FIG. 2.
Figure 4:
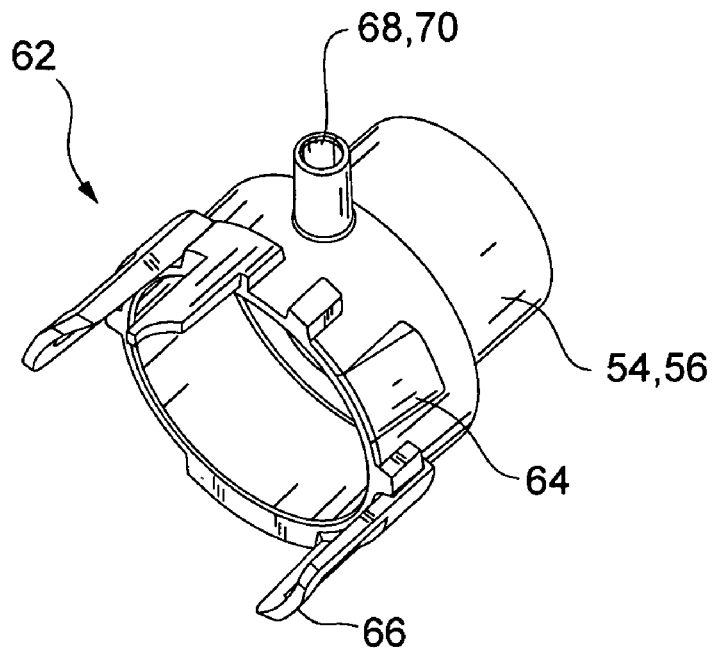
FIG. 4 is a perspective view of a portion of the housing for the flow sensor of FIG. 2.
Figure 5:
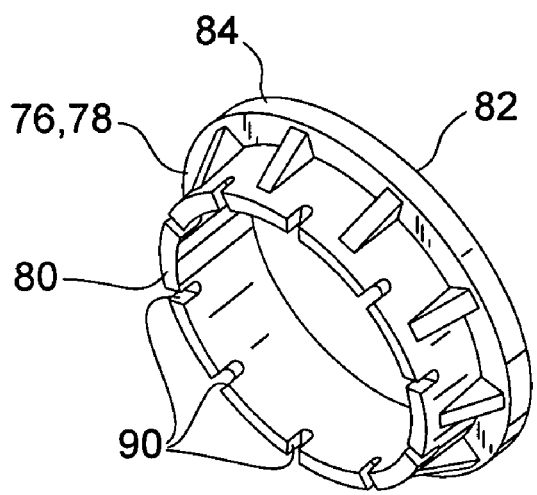
FIG. 5 is a perspective view of an averaging ring for use in the flow sensor of FIG. 2.

It is to be understood, however, that the present invention contemplates other techniques for joining the first and second housing portions in addition to the specific structure shown in FIGS. 2–4 and is not intended to be limited to the specific embodiment shown. Nevertheless, it is preferable if the means for joining the two housing portions are contained entirely on those portions. The present invention further contemplates providing alignment structures 67 that ensure the housing portions are correctly positioned with respect to one another.

Housing 52 includes a first port 68 disposed on first housing portion 54 and a second port 70 disposed on second housing portion 56. As perhaps best shown in FIG. 7, first and second ports 68 and 70 provide a fluid communication between a sensor element 72 and main channel 58. Sensor element 72 is any conventional device for measuring flow, such as a mass flow sensor or a differential pressure sensor. First port 68 provides a fluid communication between sensor element 72 and main channel 58 on a first side of a flow resistive element 74, and second port 70 provides a fluid communication between sensor element 72 and main channel 58 on a second side of flow resistive element 74 opposite the first side.

In a preferred embodiment of the present invention, the first and second ports are disposed in the same side of the housing, i.e., on the same side of the longitudinal axis, and have the same general configuration to ensure an accurate flow measurement. It is to be understood, however, other configurations for these ports are contemplated by the present invention, so long as the function of providing a fluid communication between the main channel on either side of the flow resistive element and the flow sensor element is achieved.

Flow sensor 50 also includes a first averaging ring 76 disposed on the first side of flow resistive element 74 and a second averaging ring 78 disposed on the second, opposite side of the flow resistive element. First and second averaging rings 76 and 78 serve several purposes. They each have a first end 80 that engages a wall within the housing and a second end 82 that engages the flow resistive element. In this way, the averaging rings serve to position the flow resistive element within the housing properly. The flow averaging rings also have a peripheral surface 84 that is adapted to seal against an outer wall of the housing. Preferably, the first and second averaging rings are sized and configured to hold the flow resistive element snugly within the housing and to minimize and gas leaks around the averaging rings. In addition, they are preferably made from a flexible material that provides a good seal against gas leakage, such as silicone or rubber.

Figure 7:
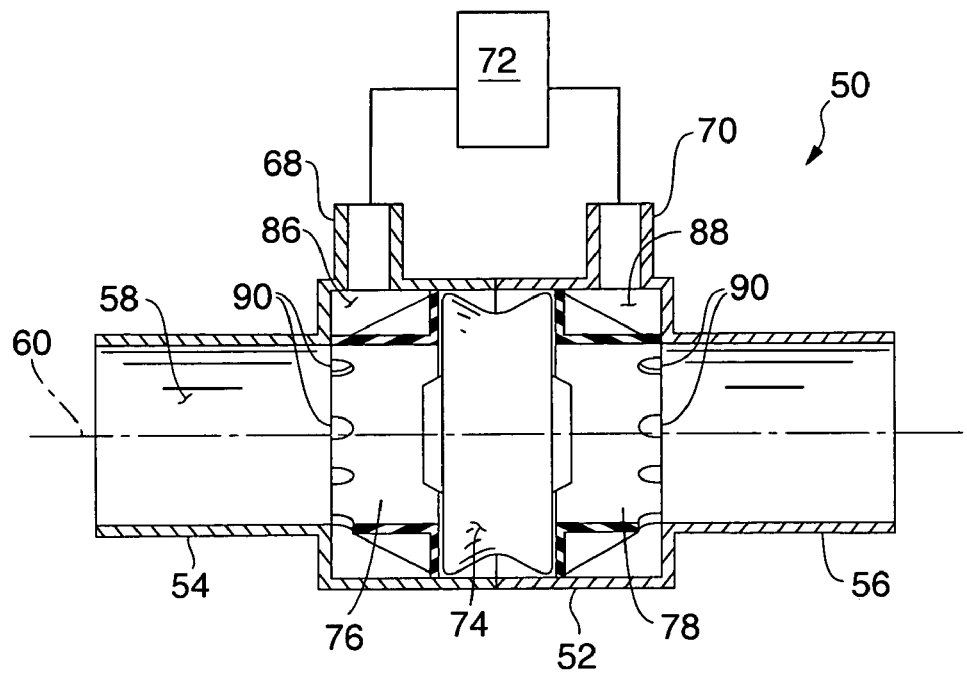
FIG. 7 is a cross-sectional view of the flow sensor of FIG. 2 taken along line 7—7 of FIG. 2.

When assembled, which is shown in FIG. 7, flow sensor 50 includes a first chamber 86 defined between first averaging ring 76 and a portion of the housing on a first side of the flow resistive element. A second chamber 88 is defined between second averaging ring 78 and a portion of the housing on the second side of the flow resistive element.

First port 68 communicates with first chamber 86 and second port 70 communicates with second chamber 88. The first and second averaging rings include a plurality of openings 90 to communicate first and second chambers 86, 88 with main channel 58.

In the illustrated embodiment, openings 90 are provided at a peripheral edge of the averaging rings and are provided around the entire perimeter of the averaging ring. By providing openings 90 about the perimeter of the averaging rings, the pressure or flow of gas existing in first and second chambers 86 and 88 represents an average of the pressure or flow of fluid within the main channel, rather than taking the pressure from one location in the main channel, which is why these rings are referred to as "averaging" rings. It is to be understood, however, that openings 90 can be provided at other locations on the averaging rings, can have other shapes and sizes, and need not be provided around the entire perimeter of the ring, so long as they provide a fluid communication between chambers 86 and 88 and the main channel.

Figure 6A:
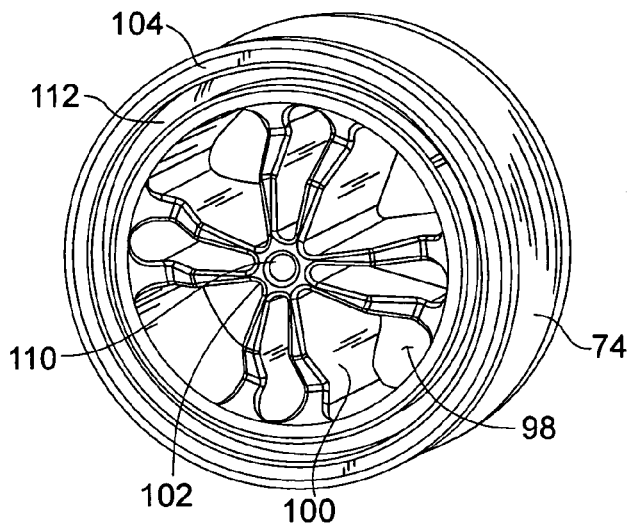
FIGS. 6A and 6B are perspective and front views, respectively, of a first embodiment of a flow restrictive element for use in the flow sensor of FIG. 2.
Figure 6B:
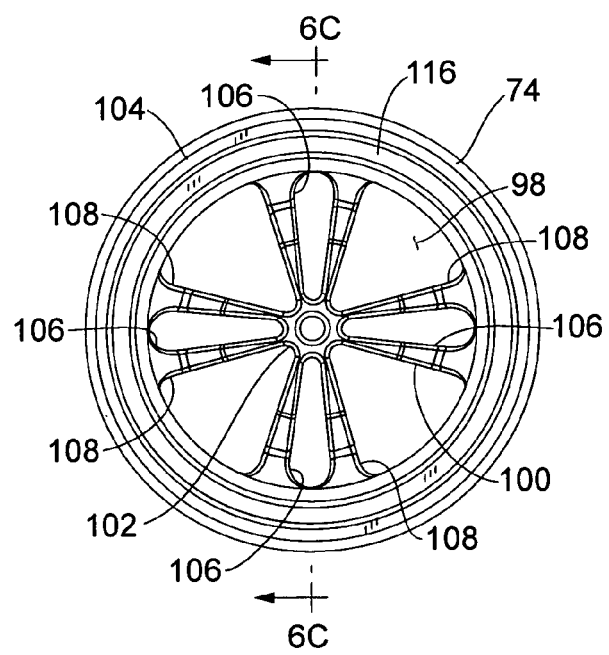
Figure 6C:
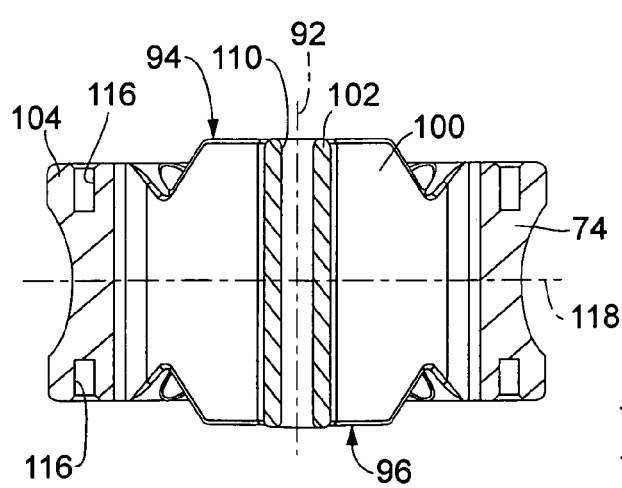
FIG. 6C is a cross-sectional view of the flow restrictive element taken along line 6C—6C of FIG. 6B.

The details of flow resistive element 74 will now be discussed below with specific reference to FIGS. 6A–6C, which show first embodiment of the flow resistive element, and with continuing reference to FIGS. 2, 3 and 7. For ease of illustration, flow resistive element 74 is not shown in section in FIG. 7, while the other components of the flow sensor, i.e., housing portions 54 and 56 and averaging rings 76 and 78, are shown in section.

As noted above, flow resistive element 74 is disposed in the housing so as to traverse main channel 58. In the preferred illustrated exemplary embodiment, a longitudinal axis 92 of the flow resistive element is aligned (coaxial) with longitudinal axis 60 of main channel 58. Flow resistive element 74 provides a slight resistance to the flow of fluid through the main channel, thereby creating a pressure drop on either side of the flow resistive element. This pressure drop enables the flow of fluid through the flow sensor to be measured by sensing element 72 using any conventional technique.

Flow resistive element 74 includes a rigid body member having a first surface 94 and a second surface 96. A plurality of unobstructed, wedge-shaped, openings 98 are defined in the flow resistive element and extend through the body member from first surface 94 to second surface 96. In the preferred illustrated exemplary embodiment, the plurality of wedge-shaped openings are defined through the body member in a direction that is substantially parallel to longitudinal axis 60 of main channel 59. It is through these wedge-shaped opening that the flow of fluid through the main channel passes. Because the body member is made from a rigid material, the area of each wedge-shaped opening does not change.

A plurality of spokes 100 extend from a central portion 102 to a perimeter portion 104 of the body member. Each spoke 100 separates adjacent wedge-shaped openings 98 from one another. In the illustrated embodiment, each spoke 100 has the same shape and size. However, the radial distance between the spoke varies so that there are two different sets of wedge-shaped openings, each set having a different size. More specifically, plurality of wedge-shaped opening 98 include a first set of first wedge-shaped openings 106, each having a first area, and a second set of second wedge-shaped openings 108, each having a second area that is greater than the first area. The first and second sets of wedge-shaped openings are arranged such that adjacent second wedge-shaped openings are separated from one another by at least one first wedge-shaped opening. Thus, there is an alternating pattern of large and small wedge-shaped openings.

By providing the above-described features for the flow element, the flow resistive element of the present invention provides a relatively laminar the flow of fluid passing through the wedge-shaped openings. Stated another way, wedge-shaped openings 98 allow the flow of fluid to exist these openings in a relatively laminar fashion. This minimized errors in flow measurements due to turbulent flow.

Flow restrictive element 74 includes a central opening 110 defined through the rigid body member generally at central portion 102. In an exemplary embodiment of the present invention, central opening 110 has a generally circular shape and is defined through the rigid body member in a direction that is substantially parallel to longitudinal axis 60 of main channel 58, and is preferably coaxial with longitudinal axis 60.

It should be noted that central opening 110 can have shapes and sizes other than those shown in the figures. In addition, the present invention contemplates eliminating central opening 110 entirely. FIG. 8 is a chart illustrating the relationship between the differential pressure created across the flow restrictive element and the flow of fluid through the flow sensor. More specifically, curve 112 is the pressure-flow relationship for the flow sensor with the central hole, and curve 114 is the pressure-flow relationship for the flow sensor without central opening 110. It can be appreciated from FIG. 8, that there is very little difference in the pressure-flow relation with and without central opening. In fact, eliminating central opening 110 improves the pressure-flow relationship, i.e., makes it more linear.

The present invention contemplates providing other features on flow resistive element 74. For example, a peripheral channel 116 can be provided at the perimeter of the flow resistive element to assist in positioning the element within the housing.

In addition, flow resistive element 74 is shown in the figures as having a symmetrical shape about a central axis 118, i.e., first surface 94, second surface 96, and the surfaces of the spokes on each side of the element are identical. This is done so that the flow resistive element provides the same pressure-flow relationship regardless of the direction of flow through the element. Those skilled in the art can appreciate, however, that the flow resistive element need not have the same surface pattern on each face, but it will only be useful to measure flow in one direction. The edges of the flow resistive element, especially at first surface 94 and second surface 96, are preferably beveled or curved to maximize their aerodynamic performance, so that fluid flows smoothly through the flow resistive element.

Figure 9A:
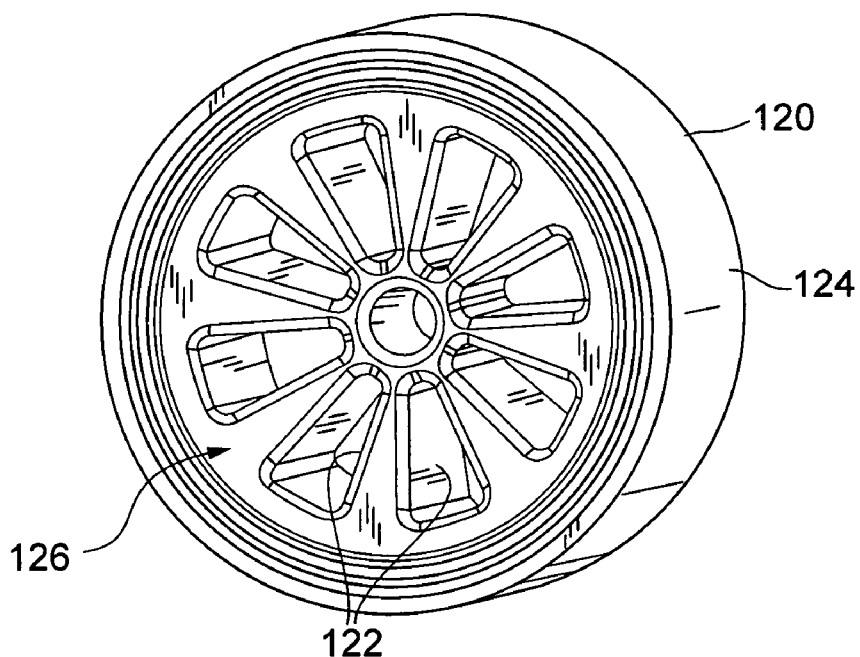
FIGS. 9A and 9B are perspective and front views, respectively, of a second embodiment of a flow restrictive element for use in the flow sensor of FIG. 2
Figure 9B:
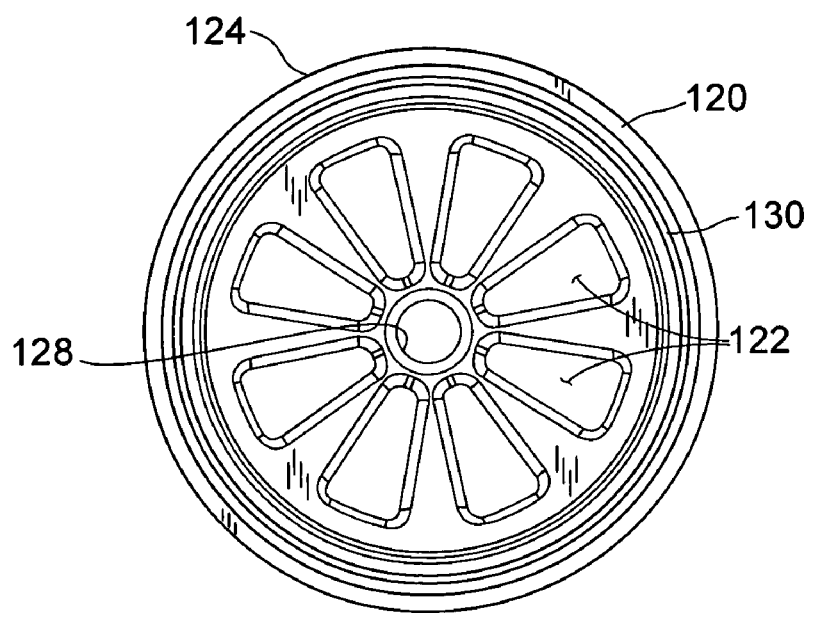

FIGS. 9A and 9B illustrate a second embodiment of a flow restrictive element 120 for use in the flow sensor of FIG. 2. Flow restrictive element 120, like flow restrictive element 74, includes a plurality of wedge-shaped openings 122 defined through a rigid body member 124. However, in the embodiment of FIGS. 9A and 9B, all of the wedge-shaped openings are uniform in size and shape. That is, all of the wedge shaped openings have the same dimensions and are uniformly spaced about a central portion of body member 124.

Flow restrictive element 120 also differs from flow restrictive element 74 in that a first surface 126 and a second surface (not shown) which is on the other side of the flow element, are substantially planar. There are no peaks and valleys in these surfaces, as is the case with the first and second surface of flow element 74.

Flow restrictive element 120 is located in the housing in the same position as flow element 74 and in the same manner. Flow restrictive element also includes an optional central opening 128 and peripheral channel 130 for positioning the element within the housing. It should be understood that the present invention contemplates other sizes for the wedge-shaped openings, other dimensions, and using different numbers of openings other than the eight openings shown in the figures.

FIGS. 10–14 illustrate a second embodiment of a flow sensor 140 according to the principles of the present invention. Flow sensor 140 differs from flow sensor 50 discussed above in the configuration of a housing 142 that contains the components of the sensor. As a result of this different configuration of housing 142, which is discussed in detail below, flow sensor 140 eliminates the need for the averaging rings used in flow sensor 50.

Housing 142 is defined by a first housing portion 144 and a second housing portion 146 that are adapted to be coupled together. These housing portions define a main channel 148 that extends along a longitudinal axis 150 through the housing between the ends thereof. A flow restrictive element, which can be either of the flow restrictive elements 74 or 120 discussed above, is sandwiched between the two housing portions and held in place between these housing portions. Thus, there is no need for a separate element, such as the averaging rings, to position and hold the flow restrictive element in place in the main channel of the flow sensor.

First housing portion 144 includes a first wall 148 disposed on the first side of flow resistive element 120. Wall 148 and an outside wall 150 of first housing portion 144 define a first chamber 152 on a first side of the flow resistive element. In addition, one side of first chamber 152 is defined by the outside wall of the first housing and the opposite side of the first chamber is blocked or sealed off by flow resistive element 74, 120.

A similar chamber structure exists on the second side of the flow resistive element. In particular, second housing portion 146 includes a second wall 154 disposed on the second side of flow resistive element 120. Wall 154 and an outside wall 156 of second housing portion 146 define a second chamber 158 on the second side of the flow resistive element. In addition, one side of second chamber 158 is defined by the outside wall of the second housing and the opposite side of the second chamber is blocked or sealed off by flow resistive element 74, 120.

First chamber 152 communicates with main channel 148 via first chamber communication ports 160 defined in first wall 145. Similarly, second chamber 158 communicates with main channel 148 via second chamber communication ports 162 defined in second wall 154. A first port 164 communicates first chamber 152 with a sensor element, such as sensor element 72 discussed above, and a second port 166 communicates second chamber 158 with the sensor element. An opening 168 in outside wall 150 where first port 164 communicates with first chamber 152 is visible in FIG. 12 and is shown in dashed lines in FIG. 14. Similarly, an opening 170 in outside wall 156 where second port 166 communicates with second chamber 155 is visible in FIG. 13 and is shown in dashed lines in FIG. 14.

As a result of this configuration for flow sensor 140, first and second chambers 152 and 158 are isolated from one another on opposite sides of flow resistive element 74, 120, while still in fluid communication with the main channel on each side of the flow resistive element, respectively. Thus, first and second chambers 152 and 158 are similar in function to first and second chambers 86 and 88 in the prior embodiment. In addition, the first and second chamber communication ports 160 and 162 provide a similar function as the ports in the averaging rings of the previous embodiment. Namely, by communicating the first and second chambers with the main channel at more than one location, errors due to turbulent flow in the main chamber are minimized.

In a presently preferred embodiment, first chamber communication ports 160, second chamber communication ports 162, first port 164, and second port 166 are all disposed on the same side of longitudinal axis 150 of the flow sensor. This configuration prevents any moisture that may build up in main channel 148 from entering first or second chambers 152 or 158. In addition, by providing first and second ports 164 and 166 on the same side of the longitudinal axis as ports 160 and 162, any moisture that may enter first and second chambers 152 and 158 is kept away from first and second ports 164 and 166, so long as the flow sensor is maintained in a position where the first and second ports are located at or near the highest point on the sensor. This is easily accomplished by positioning flow sensor 140 in the pressure support system in the orientation shown in FIG. 10, i.e., so that ports 164 and 166 are at the top of the sensor.

It is to be understood that other configurations for ports 160, 162, 164 and 166 are contemplated by the present invention, so long as the function of providing a fluid communication between the main channel on either side of the flow resistive element and the flow sensor element is achieved. For example, more than two ports 160 or 162 can be provided on walls 148 and 154. The shape, size and location of ports 160 can also be altered, perhaps to improve the pressure averaging function of such ports. Ports 164 and 166 can be oriented in a vertical direction, i.e., aligned such that the longitudinal axis of these ports bisects longitudinal axis 150, rather than the tangential orientation shown in the figures.

First housing portion 144 and second housing portion 146 are maintained in an engaged relation by a locking assembly, generally indicated at 172, that couples these two portions together in the same manner locking assembly 62 joins the housing portions in the previous flow sensor embodiment. In the illustrated embodiment, locking assembly 172 is a snap-type, male-female configuration, where a locking portion 174 inserts into a receiving member 176, and is maintained in the engaged relation due to locking grooves and protrusions provided in locking portion 174 and receiving members 176.

Figure 14:
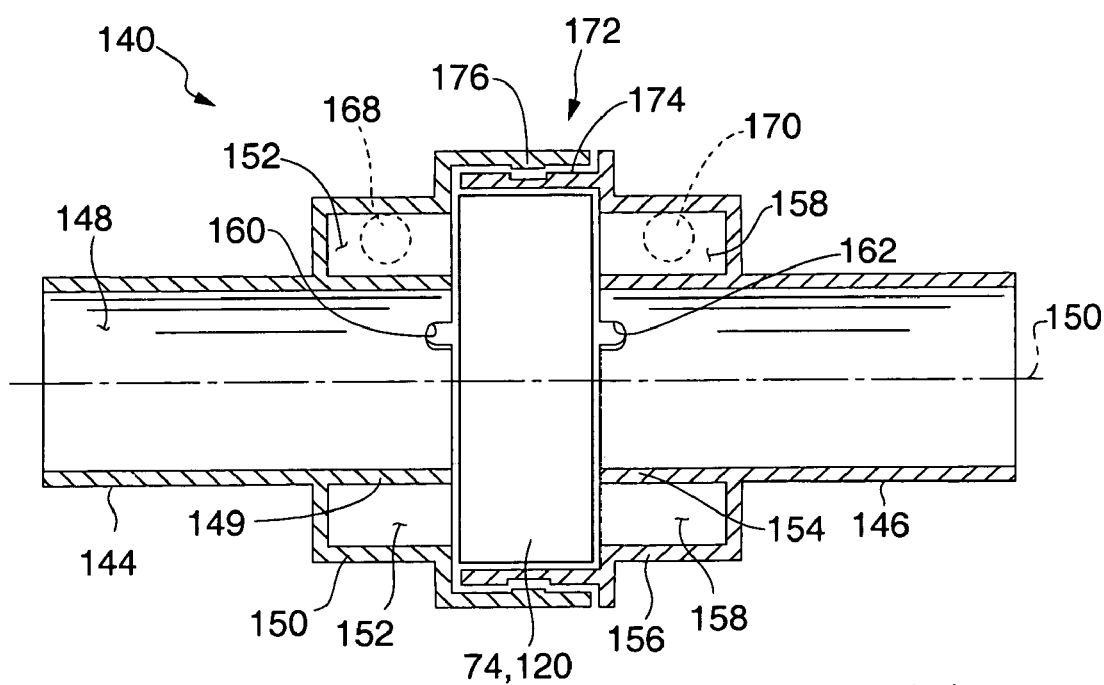
FIG. 14 is a cross-sectional view of the flow sensor of FIG. 10 taken along line 14—14 of FIG. 10.
Figure 12:
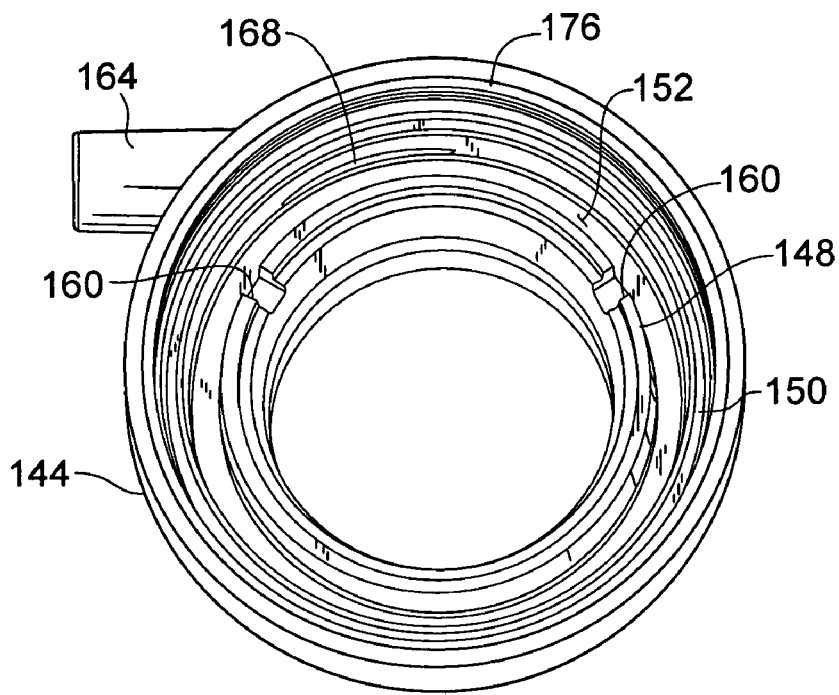
FIG. 12 is a perspective view showing the interior of a female portion of the housing for the flow sensor of FIG. 10.
Figure 13:
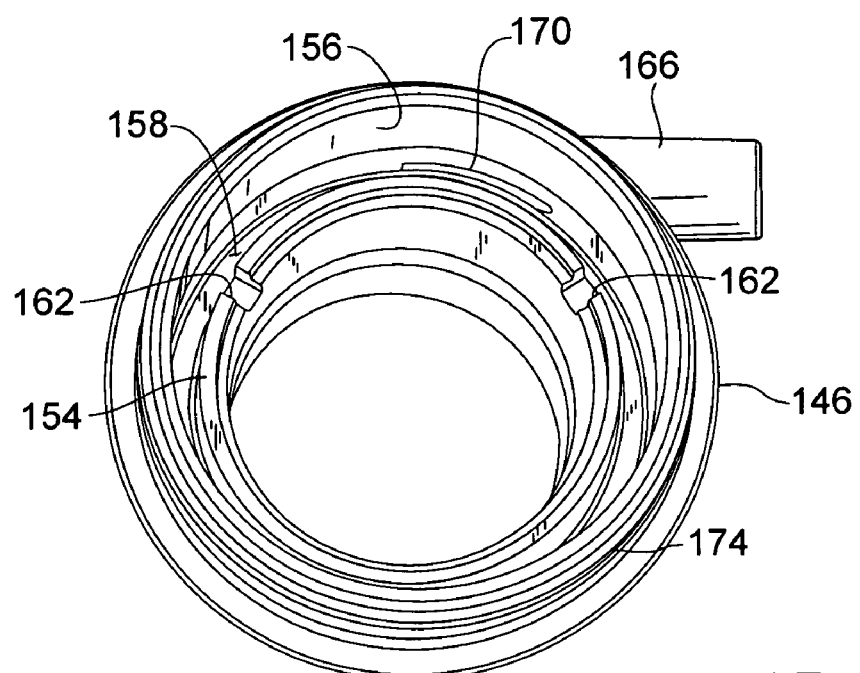
FIG. 13 is a perspective view showing the interior of a male portion of the housing for the flow sensor of FIG. 10.

It is to be understood that the present invention contemplates other techniques for joining first and second housing portions 144 and 146 in addition to the specific structure shown in FIGS. 12–14 and is not intended to be limited to the specific embodiment shown. For example, the locking assembly of FIGS. 2–4 can be used in place of locking assembly 172. Likewise, locking assembly 172 can be interchanged with locking assembly 62. Of course, such interchanging of locking assembly would require reconfiguring the structures for the housing. In any event, it is preferable if the means for joining the two housing portions are contained entirely on those portions, as is the case with either locking assembly discussed herein.

Figure 10:
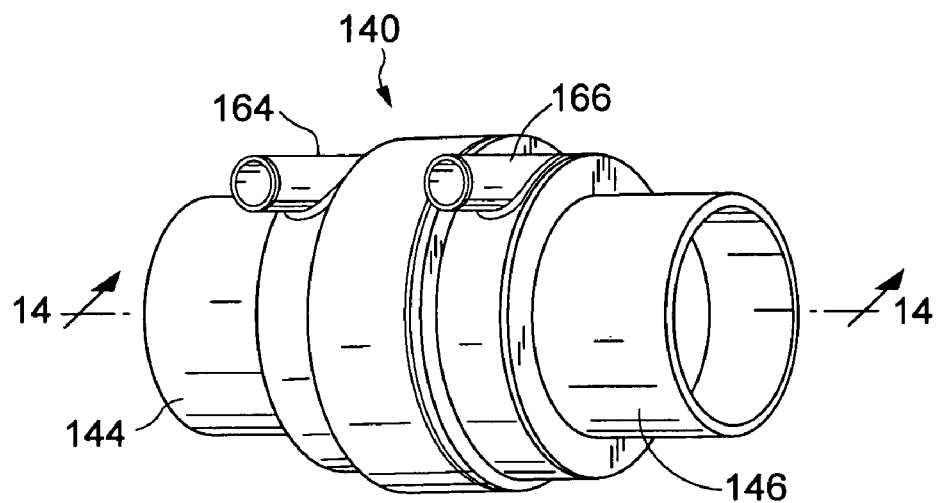
FIG. 10 is a perspective view of a second embodiment of a flow sensor according to the principles of the present invention.
Figure 11:
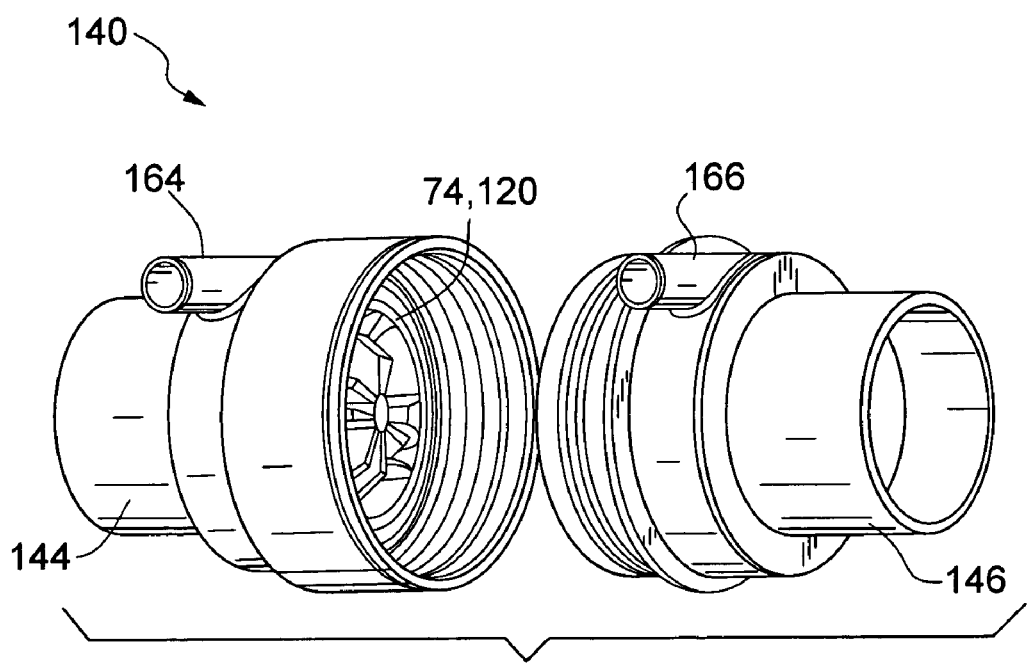
FIG. 11 is an exploded view of the flow sensor of FIG. 10.
Figure 15:
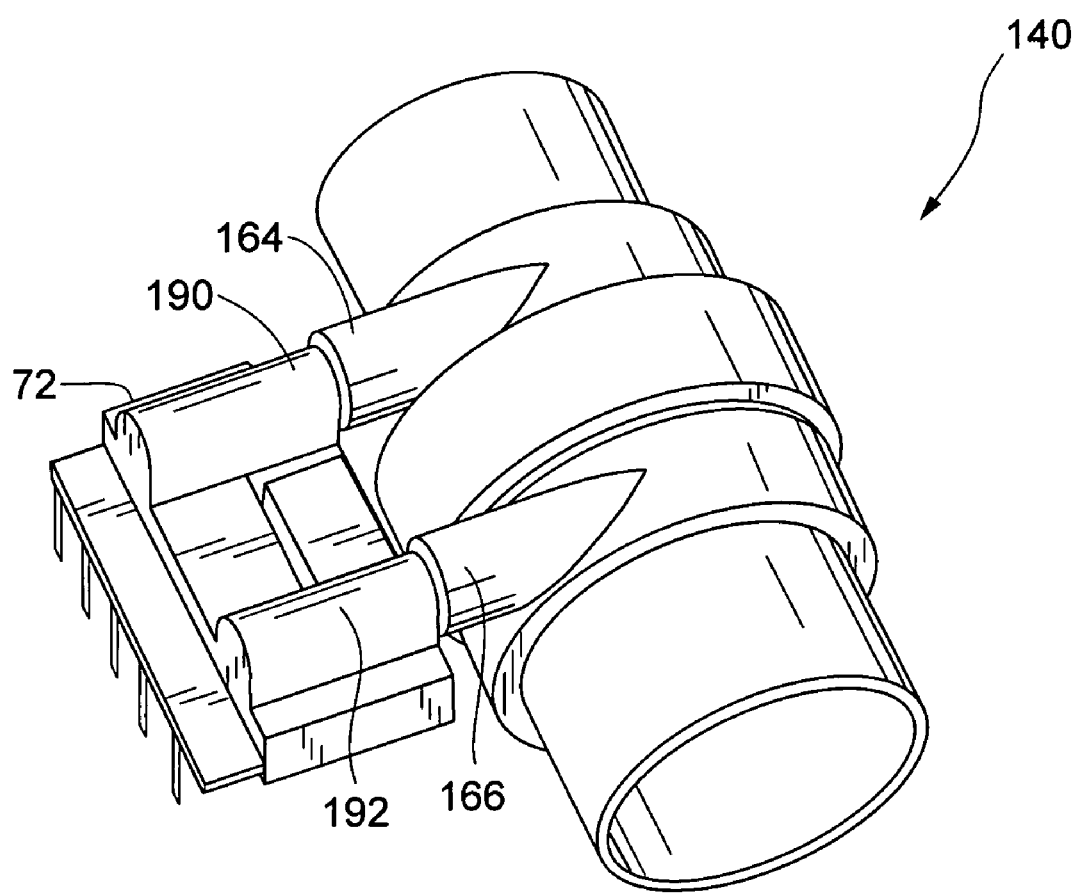
FIG. 15 is a perspective view of the flow sensor of FIG. 10 connected directly to a sensor element.

As noted above, the present invention contemplates coupling the gas communication ports, such as ports 164 and 166 in the embodiment shown in FIG. 10, to a sensor element 72 (See FIG. 7) via a length tubing having one end connected to the port and the other end connected to a portion of the sensor element. However, the present invention also contemplates eliminating the length of tubing by connecting the ports in the flow sensor directly to the sensing element, as example of which is shown in FIG. 15. As shown in this figure, ports 164 and 166 are coupled directly to ports 190 and 192 in sensor element 72. In this illustrated exemplary embodiment, sensor element 72 is a conventional integrated circuit containing pressure sensors for detecting/measuring the flow of gas through flow sensor 140.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A flow sensor adapted to be positioned in a fluid carrying conduit to measure a flow of fluid passing through the conduit, comprising:
   (1) a housing having a first end, a second end, and a main channel defined through the housing between the first end and the second end, wherein the main channel includes a longitudinal axis, and wherein the first and the second ends of the housing are adapted to be coupled to the conduit so that fluid passes through the housing along the main channel between the first end and the second end;
   (2) a flow resistive element coupled to the housing such that the flow resistive element does not rotate relative to the housing and traverses the main channel, wherein the flow resistive element comprises:
      (a) a rigid body member fixed to the housing and having a first surface and a second surface,
      (b) a plurality of unobstructed, wedge-shaped, openings defined in the body member and extending therethrough from the first surface to the second surface, and
      (c) a plurality of spokes extending from a central portion of the body member to a perimeter thereof, wherein each spoke separates adjacent wedge-shaped openings from one another;
   (3) a first port defined through the housing to communicate a sensor element with the main channel on a first side of the flow resistive element; and
   (4) a second port defined through the housing to communicate the sensor element with the main channel on a second side of the flow resistive element opposite the first side.

2. The flow sensor of claim 1, wherein the plurality of wedge-shaped openings are uniform in size and shape.

3. The flow sensor of claim 1, wherein the plurality of wedge-shaped openings are defined through the body member in a direction that is substantially parallel to the longitudinal axis of the main channel.

4. The flow sensor of claim 1, wherein the first surface is substantially planar and is disposed in a first plane that is substantially perpendicular to the longitudinal axis, and wherein the second surface is substantially planar and is disposed in a second plane that is also substantially perpendicular to the longitudinal axis.

5. The flow sensor of claim 1, wherein each wedge-shaped opening in the plurality of wedge-shaped openings includes an apex portion, and wherein the plurality of wedge-shaped openings are defined in the rigid body member such that the apexes of the plurality of wedge shaped openings are located proximate to a center of the rigid body member.

6. The flow sensor of claim 1, wherein the plurality of wedge-shaped openings include a first set of first wedge-shaped openings each having a first area and a second set of second wedge-shaped openings each having a second area that is greater than the first area, and wherein adjacent second wedge-shaped openings are separated from one another by at least one first wedge-shaped opening.

7. The flow sensor of claim 1, further comprising a central opening defined through the rigid body member generally at a central location of the rigid body.

8. The flow sensor of claim 7, wherein the central opening has a generally circular shape and is defined through the rigid body member in a direction that is substantially parallel to the longitudinal axis of the main channel.

9. The flow sensor of claim 1, wherein the housing comprises a first housing portion and a second housing portion having an identical structure, and wherein the first and the second housing portions include an locking assembly that selectively couples the first housing portion to the second housing portion.

10. The flow sensor of claim 1, further comprising a first averaging ring disposed on the first side of the flow resistive element such that a first chamber is defined between the first averaging ring and a portion of the housing, and a second averaging ring disposed on a second side of the flow resistive element such that a second chamber is defined between the first averaging ring and a portion of the housing, wherein the first port communicates with the first chamber and the second port communicates with the second chamber, and wherein the first and the second averaging rings include a plurality of openings defined therein to communicate the first and the second chambers with the main channel.

11. The flow sensor of claim 1, further comprising:
a first wall disposed on the first side of the flow resistive element, wherein the first wall defines a first chamber on the first side of the flow resistive element, wherein the first chamber communicates with the main channel via at least one first chamber communication port defined in the first wall, and wherein the first port communicates with the first chamber; and
a second wall disposed on the second side of the flow resistive element, wherein the second wall defines a second chamber on the second side of the flow resistive element, wherein the second chamber communicates with the main channel via at least one second chamber communication port defined in the second wall, and wherein the second port communicates with the second chamber.

12. The flow sensor of claim 11, wherein the first chamber communication port, the second chamber communication port, the first port, and the second port are all disposed on one side of the longitudinal axis of the flow sensor.

13. A flow resistive element comprising:
a rigid body member having a first surface and a second surface and a longitudinal axis,
a plurality of unobstructed, wedge-shaped, openings defined in the body member and extending therethrough from the first surface to the second surface, and
a plurality of spokes extending from a central portion of the body member to a perimeter thereof, wherein each spoke separates adjacent wedge-shaped openings from one another, wherein the plurality of wedge-shaped openings include a first set of first wedge-shaped openings each having a first area and a second set of second wedge-shaped openings each having a second area that is greater than the first area, and wherein adjacent second wedge-shaped openings are separated from one another by at least one first wedge-shaped opening.

14. The flow resistive element of claim 13, wherein the plurality of wedge-shaped openings are uniform in size and shape.

15. The flow resistive element of claim 13, wherein the plurality of wedge-shaped openings are defined through the body member in a direction that is substantially parallel to the longitudinal axis of the body member.

16. The flow resistive element of claim 13, wherein the first surface is substantially planar and is disposed in a first plane that is substantially perpendicular to the longitudinal axis, and wherein the second surface is substantially planar and is disposed in a second plane that is also substantially perpendicular to the longitudinal axis.

17. The flow resistive element of claim 13, wherein each wedge-shaped opening in the plurality of wedge-shaped openings includes an apex portion, and wherein the plurality of wedge-shaped openings are defined in the rigid body member such that the apexes of the plurality of wedge shaped openings are located proximate to a center of the rigid body member.

18. The flow resistive element of claim 13, further comprising a central opening defined through the rigid body member generally at a central location of the rigid body.

19. The flow resistive element of claim 18, wherein the central opening has a generally circular shape and is defined through the rigid body member in a direction that is substantially parallel to the longitudinal axis of the main channel.

20. A flow sensor adapted to be positioned in a fluid carrying conduit to measure a flow of fluid passing through the conduit, comprising:
(1) a housing having a first end, a second end, and a main channel defined through the housing between the first end and the second end, wherein the main channel includes a longitudinal axis, and wherein the first and the second ends of the housing are adapted to be coupled to the conduit so that fluid passes through the housing along the main channel between the first end and the second end; and
(2) a flow resistive element disposed in the housing so as to traverse the main channel, wherein the flow resistive element comprises:
(a) a rigid body member having a first surface and a second surface,
(b) a plurality of unobstructed, wedge-shaped, openings defined in the body member and extending therethrough from the first surface to the second surface, and
(c) a plurality of spokes extending from a central portion of the body member to a perimeter thereof, wherein each spoke separates adjacent wedge-shaped openings from one another, wherein the plurality of wedge-shaped openings include a first set of first wedge-shaped openings each having a first area and a second set of second wedge-shaped openings each having a second area that is greater than the first area, and wherein adjacent second wedge-shaped openings are separated from one another by at least one first wedge-shaped opening.

21. A flow sensor adapted to be positioned in a fluid carrying conduit to measure a flow of fluid passing through the conduit, comprising:
(1) a housing having a first end, a second end, and a main channel defined through the housing between the first end and the second end, wherein the main channel includes a longitudinal axis, and wherein the first and the second ends of the housing are adapted to be coupled to the conduit so that fluid passes through the housing along the main channel between the first end and the second end;
(2) a flow resistive element disposed in the housing so as to traverse the main channel, wherein the flow resistive element comprises:
  (a) a rigid body member having a first surface and a second surface,
  (b) a plurality of unobstructed, wedge-shaped, openings defined in the body member and extending therethrough from the first surface to the second surface, and
  (c) a plurality of spokes extending from a central portion of the body member to a perimeter thereof, wherein each spoke separates adjacent wedge-shaped openings from one another;
(3) a first port defined through the housing to communicate a sensor element with the main channel on a first side of the flow resistive element;
(4) a second port defined through the housing to communicate the sensor element with the main channel on a second side of the flow resistive element opposite the first side;
(5) a first averaging ring disposed on the first side of the flow resistive element such that a first chamber is defined between the first averaging ring and a portion of the housing; and
(6) a second averaging ring disposed on a second side of the flow resistive element such that a second chamber is defined between the first averaging ring and a portion of the housing, wherein the first port communicates with the first chamber and the second port communicates with the second chamber, and wherein the first and the second averaging rings include a plurality of openings defined therein to communicate the first and the second chambers with the main channel.

22. A flow sensor adapted to be positioned in a fluid carrying conduit to measure a flow of fluid passing through the conduit, comprising:
(1) a housing having a first end, a second end, and a main channel defined through the housing between the first end and the second end, wherein the main channel includes a longitudinal axis, and wherein the first and the second ends of the housing are adapted to be coupled to the conduit so that fluid passes through the housing along the main channel between the first end and the second end;
(2) a flow resistive element disposed in the housing so as to traverse the main channel, wherein the flow resistive element comprises:
  (a) a rigid body member having a first surface and a second surface,
  (b) a plurality of unobstructed, wedge-shaped, openings defined in the body member and extending therethrough from the first surface to the second surface, and
  (c) a plurality of spokes extending from a central portion of the body member to a perimeter thereof, wherein each spoke separates adjacent wedge-shaped openings from one another,
(3) a first port defined through the housing to communicate a sensor element with the main channel on a first side of the flow resistive element;
(4) a second port defined through the housing to communicate the sensor element with the main channel on a second side of the flow resistive element opposite the first side;
(5) a first wall disposed on the first side of the flow resistive element, wherein the first wall defines a first chamber on the first side of the flow resistive element, wherein the first chamber communicates with the main channel via at least one first chamber communication port defined in the first wall, and wherein the first port communicates with the first chamber; and
(6) a second wall disposed on the second side of the flow resistive element, wherein the second wall defines a second chamber on the second side of the flow resistive element, wherein the second chamber communicates with the main channel via at least one second chamber communication port defined in the second wall, and wherein the second port communicates with the second chamber.

* * * * *